(12) United States Patent
McCullough

(10) Patent No.: US 9,266,910 B2
(45) Date of Patent: Feb. 23, 2016

(54) ASYMMETRIC POLYPROPYLENE CATALYSTS

(71) Applicant: ExxonMobil Chemical Patents Inc., Baytown, TX (US)

(72) Inventor: Laughlin G. McCullough, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/511,806

(22) Filed: Oct. 10, 2014

(65) Prior Publication Data

US 2015/0119539 A1    Apr. 30, 2015

Related U.S. Application Data

(60) Provisional application No. 61/896,957, filed on Oct. 29, 2013.

(51) Int. Cl.

| C07F 17/00 | (2006.01) |
|---|---|
| C08F 4/6592 | (2006.01) |
| C08F 4/642 | (2006.01) |
| C08F 110/06 | (2006.01) |
| C08F 210/06 | (2006.01) |
| C07F 7/00 | (2006.01) |
| C08F 4/659 | (2006.01) |

(52) U.S. Cl.
CPC . *C07F 7/00* (2013.01); *C07F 17/00* (2013.01); *C08F 4/65927* (2013.01); *C08F 110/06* (2013.01); *C08F 210/06* (2013.01); *C08F 4/65912* (2013.01); *C08F 4/65916* (2013.01)

(58) Field of Classification Search
CPC .. C07F 17/00; C08F 4/65912; C08F 4/65916; C08F 4/65927; C08F 110/06; C08F 210/06
See application file for complete search history.

(56) References Cited

U.S. PATENT DOCUMENTS

| 5,416,177 | A | 5/1995 | Siedle et al. |
|---|---|---|---|
| 5,817,590 | A | 10/1998 | Hasegawa et al. |
| 6,342,566 | B2 | 1/2002 | Burkhardt et al. |
| 6,355,747 | B1 | 3/2002 | Rausch et al. |
| 6,384,142 | B1 | 5/2002 | Burkhardt et al. |
| 6,472,474 | B2 | 10/2002 | Burkhardt et al. |
| 6,960,676 | B2 | 11/2005 | Rix et al. |
| 7,081,543 | B2 | 7/2006 | Rix et al. |
| 7,101,940 | B2 | 9/2006 | Schottek et al. |
| 7,531,605 | B2 | 5/2009 | Machida et al. |
| 7,741,417 | B2 | 6/2010 | Casty et al. |
| 7,851,644 | B2 | 12/2010 | Ewen et al. |
| 8,076,419 | B2 | 12/2011 | Meka et al. |
| 8,202,958 | B2 | 6/2012 | Demirors et al. |
| 2003/0013913 | A1 | 1/2003 | Schottek et al. |
| 2005/0261449 | A1 | 11/2005 | Voskoboynikov et al. |
| 2007/0135597 | A1 | 6/2007 | Voskoboynikov et al. |
| 2008/0242812 | A1 | 10/2008 | Ruchatz et al. |
| 2010/0152388 | A1 | 6/2010 | Jiang et al. |
| 2011/0172375 | A1 | 7/2011 | Yeh et al. |
| 2013/0023633 | A1 | 1/2013 | Holtcamp et al. |
| 2013/0150541 | A1 | 6/2013 | Crowther et al. |
| 2014/0179872 | A1* | 6/2014 | Fiscus et al. .......... 525/240 |
| 2014/0179884 | A1* | 6/2014 | McCullough ........ 526/126 |
| 2014/0194277 | A1* | 7/2014 | Ishihama et al. ........ 502/117 |

FOREIGN PATENT DOCUMENTS

| EP | 0 277 004 A1 | 8/1988 |
|---|---|---|
| EP | 0 405 201 A2 | 1/1991 |
| EP | 0 630 910 A1 | 12/1994 |
| EP | 0 798 306 A1 | 10/1997 |
| WO | WO 91/02012 A1 | 2/1991 |
| WO | WO 01/48035 A2 | 7/2001 |
| WO | WO 01/62764 A1 | 8/2001 |
| WO | WO 01/68718 A1 | 9/2001 |
| WO | WO 02/02576 | 1/2002 |
| WO | WO 03/035708 A1 | 5/2003 |
| WO | WO 2004/005360 A2 | 1/2004 |
| WO | WO 2014/099303 | 6/2014 |

OTHER PUBLICATIONS

Giardello et al., "*Chiral $C_1$-Symmetric Group 4 Metallocenes as Catalysts for Stereoregular α-Olefin Polymerization. Metal, Ancillary Ligand, and Counteranion Effects*," J. Am. Chem. Soc. 1995, vol. 117, pp. 12114-12129.

Sanginov et al., "*Metallocene Systems in Propylene Polymerization: Effect of Triisobutylaluminum and Lewis Bases on the Behavior of Catalysts and Properties of Polymer*," Polymer Science, Series A (2006), vol. 48, No. 2, pp. 99-106.

Martinez et al., "*Polymerization Activity Prediction of Zirconocene Single-Site Catalysts Using 3D Quantitative Structure-Activity Relationship Modeling*," Organometallics, vol. 31, No. 5, Mar. 12, 2012, pp. 1673-1679.

Villaseñor et al., "*Neutral Dimethylzirconocene Complexes as Initiators for the Ring-Opening Polymerization of ε-Caprolactone*," European Journal of Inorganic Chemistry, vol. 2013, Issue 7, Mar. 1, 2013, pp. 1184-1196.

* cited by examiner

*Primary Examiner* — Caixia Lu

(57) ABSTRACT

This invention relates to unsymmetrical metallocenes, catalyst systems therefrom and their use to make highly isotactic polypropylene.

21 Claims, No Drawings

ASYMMETRIC POLYPROPYLENE CATALYSTS

PRIORITY

This invention claims priority to and the benefit of U.S. Ser. No. 61/896,957, filed Oct. 29, 2013.

FIELD OF THE INVENTION

This invention relates to novel catalyst compounds comprising asymmetric bridged metallocenes of the type T(Cp)(Ind)MX2 (Cp=cyclopentadiene) (Ind=indenyl) (T=bridging group) and catalyst systems comprising such and uses thereof.

BACKGROUND OF THE INVENTION

Olefin polymerization catalysts are of great use in industry. Hence there is interest in finding new catalyst systems, including catalyst activators that increase the polymerization activity of the catalyst and allow the production of polymers having specific properties, such as high melting point and high molecular weight.

Catalysts for olefin polymerization are often based on metallocenes as catalyst precursors, which are activated either with the help of an alumoxane, or with an activator containing a non-coordinating anion.

Other references of interest include U.S. Pat. Nos. 5,416,177; 5,817,590; 8,202,958; 8,076,419; 7,531,605; 7,741,417, 6,355,747; 7,851,644; 7,081,543; 6,342,566; 6,960,676; 6,384,142; 6,472,474; U.S. Patent Publication Nos. 2011/0172375 and 2010/0152388; EP Patent Publication Nos. 0 277 004, 0 405 201, 0 798 306, 0 630 910; PCT Publication Nos. WO 91/02012, WO 01/62764, WO 01/68718, WO 2004/005360, WO 01/48035, WO 03/035708; M. A. Giardello, M. S. Eisen, Ch. L. Stern and T. J. Marks, J. Am. Chem. Soc. 1995, 117, pp. 12114-12129; and E. A. Sanginov, A. N. Panin, S. L. Saratovskikh, N. M. Bravaya, Polymer Science, Series A (2006), 48(2), pp. 99-106.

There is still a need in the art for new and improved catalyst systems for the polymerization of olefins, in order to achieve specific polymer properties, such as high melting point, high molecular weights, to increase conversion or comonomer incorporation, or to alter comonomer distribution without deteriorating the resulting polymer's properties.

It is therefore an object of the present invention to provide novel catalyst compounds, catalysts systems comprising such compounds, and processes for the polymerization of olefins using such compounds and systems.

SUMMARY OF THE INVENTION

This invention relates to a method to polymerize olefins comprising contacting a catalyst compound with an activator and one or more monomers. This invention further relates to novel catalyst compounds. This invention further relates to polymer compositions produced by the methods described herein.

New catalyst compositions are provided as well as catalyst systems and their use to produce polymers, such as isotactic polypropylene. The catalysts are unsymmetrical, having C1 symmetry. That is, the catalyst has no planes of symmetry about any axis. This asymmetry is advantageous as no isomers (rac/meso) are formed and so only one isomer exists, providing yield of catalyst compositions much higher than those that are symmetrical. Additionally, the catalysts provide isotactic polypropylene which is surprising since the catalyst is asymmetric. An additional unexpected advantage is that the catalyst and catalyst systems can be used to produce both polypropylene and polyethylene with high activity. Generally, metallocene catalysts are selective to either propylene or ethylene but not both.

The catalysts described herein are represented by the formula:

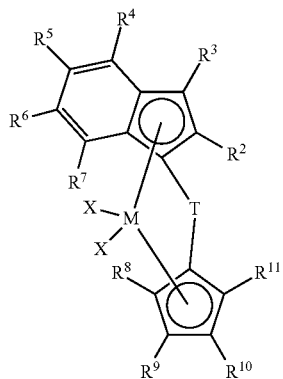

wherein

M is a transition metal atom selected from group 3, 4, or 5 of the Periodic Table of Elements;

T is a bridging group;

each X is a univalent anionic ligand, or two Xs are joined and bound to the metal atom to form a metallocycle ring, or two Xs are joined to form a chelating ligand, a diene ligand, or an alkylidene ligand;

$R^2$ is a substituted or unsubstituted $C_1$ to a $C_{20}$ hydrocarbyl group;

$R^3$, $R^5$, $R^6$ and $R^7$ are each independently a hydrogen atom or a substituted or unsubstituted $C_1$ to a $C_{20}$ hydrocarbyl group and any two of $R^5$, $R^6$, and $R^7$ adjacent to each other can be joined to form a cyclic structure;

$R^4$ is a substituted or unsubstituted aryl group; and $R^8$, $R^9$, $R^{10}$ and $R^{11}$ are each independently a substituted or unsubstituted $C_1$ to a $C_6$ hydrocarbyl group and $R^9$ and $R^{10}$ can be joined to form a cyclic structure.

In one aspect, $R^2$ is primary substituted or unsubstituted $C_1$-$C_{12}$ alkyl group such as methyl, ethyl or n-propyl.

In another aspect, $R^4$ is selected from phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

In still another aspect, R3 is a hydrogen.

In yet another aspect, T is represented by the formula, (R*2G)g, where each G is C, Si, or Ge, g is 1 or 2, and each R* is, independently, hydrogen, halogen, $C_1$ to $C_{20}$ hydrocarbyl or a C1 to C20 substituted hydrocarbyl, and two or more R* can form a cyclic structure including aromatic, partially saturated, or saturated cyclic or fused ring system.

It should be understood that any of the selections of substituents and groups noted above can be combined in any manner and are not limiting.

Additionally, the catalyst can be combined with an activator, such as methyl alumoxane and/or a non-coordinating anion to provide a catalyst system. Either the catalyst or the catalyst system can be combined with a support, such as silica and/or alumina. The catalyst system, supported or unsupported, can be used to polymerize olefins, such as propylene or ethylene.

DETAILED DESCRIPTION

For the purposes of this invention and the claims thereto, the new numbering scheme for the Periodic Table Groups is used as described in Chemical and Engineering News, 63(5), p. 27 (1985). Therefore, a "Group 4 metal" is an element from Group 4 of the Periodic Table, e.g. Hf, Ti, or Zr.

Unless otherwise indicated, "catalyst productivity" is a measure of how many grams of polymer (P) are produced using a polymerization catalyst comprising W g of catalyst (cat), over a period of time of T hours; and may be expressed by the following formula: P/(T×W) and expressed in units of gPgcat-1 hr-1. Unless otherwise indicated, "conversion" is the amount of monomer that is converted to polymer product, and is reported as mol % and is calculated based on the polymer yield and the amount of monomer fed into the reactor. Unless otherwise indicated, "catalyst activity" is a measure of how active the catalyst is and is reported as the mass of product polymer (P) produced per mole of catalyst (cat) used (kgP/molcat).

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is typically a polymer having a low molecular weight (such an Mn of less than 25,000 g/mol, preferably less than 2,500 g/mol) or a low number of mer units (such as 75 mer units or less). An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered an α-olefin.

For purposes of this invention and claims thereto, the term "substituted" means that a hydrogen group has been replaced with a heteroatom, or a heteroatom containing group. For example, a "substituted hydrocarbyl" is a radical made of carbon and hydrogen where at least one hydrogen is replaced by a heteroatom or heteroatom containing group.

As used herein, Mn is number average molecular weight, Mw is weight average molecular weight, and Mz is z average molecular weight, wt % is weight percent, and mol % is mole percent. Molecular weight distribution (MWD), also referred to as polydispersity, is defined to be Mw divided by Mn. Unless otherwise noted, all molecular weight units (e.g., Mw, Mn, Mz) are g/mol.

The following abbreviations may be used herein: Me is methyl, Et is ethyl, Pr is propyl, cPR is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, MAO is methylalumoxane, Ind is indenyl, Cp is cyclopentadienyl, Flu is fluorenyl, OTf is triflate, RT is room temperature (23° C., unless otherwise indicated).

A "catalyst system" is combination of at least one catalyst compound, at least one activator, an optional co-activator, and an optional support material. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, metallocene catalyst compound or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties.

For purposes of this invention and claims thereto in relation to metallocene catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group, ethyl alcohol is an ethyl group substituted with an —OH group.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 100 carbon atoms and which may be linear, branched, or cyclic, and when cyclic, aromatic or non-aromatic. A "substituted hydrocarbyl" is a radical made of carbon and hydrogen where at least one hydrogen is replaced by a heteroatom or heteroatom containing group.

Catalyst Compounds

This invention relates to novel catalysts represented by the formula:

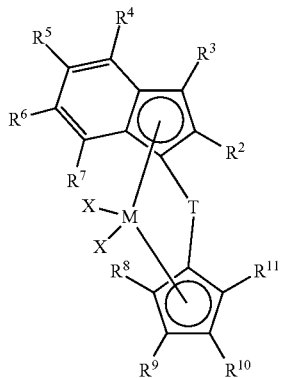

wherein

M is a transition metal atom selected from group 3, 4, or 5 of the Periodic Table of Elements, preferably a group 4 metal, preferably Hf, Ti or Zr;

T is a bridging group;

each X is a univalent anionic ligand, or two Xs are joined and bound to the metal atom to form a metallocycle ring, or two Xs are joined to form a chelating ligand, a diene ligand, or an alkylidene ligand;

$R^2$ is a substituted or unsubstituted $C_1$ to a $C_{20}$ hydrocarbyl group (such as methyl, ethyl, propyl, butyl, pentyl, hexyl, heptyl, octyl, nonyl, decyl, undecyl, or dodecyl), preferably $R^2$ is a primary substituted or unsubstituted $C_1$-$C_{12}$ alkyl group;

$R^3$, $R^5$, $R^6$ and $R^7$ are each independently a hydrogen atom or a substituted or unsubstituted $C_1$ to a $C_{20}$ alkyl group (such as methyl, ethyl, propyl, butyl, pentyl, hexyl, heptyl, octyl, nonyl, decyl, undecyl, or dodecyl) and any two of $R^5$, $R^6$, and $R^7$ adjacent to each other can be joined to form a cyclic structure, preferably $R^5$, $R^6$, and $R^7$ are independently a hydrogen atom or a substituted or unsubstituted $C_1$ to a $C_6$ hydrocarbyl group;

$R^4$ is a substituted or unsubstituted aryl group; and $R^8$, $R^9$, $R^{10}$ and $R^{11}$ are each independently a substituted or unsubstituted $C_1$ to a $C_6$ alkyl group (such as methyl, ethyl, propyl, butyl, pentyl, or hexyl) and $R^9$ and $R^{10}$ can be joined to form a cyclic structure.

In one aspect, in any embodiment of any formula described herein, each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and C1 to C5 alkyl groups, preferably each X is a methyl group. Preferably X is selected from chloro, bromo, methyl, ethyl, propyl, butyl, pentyl, hexyl, heptyl, octyl, nonyl, decyl, undecyl, and dodecyl.

In another aspect, in any embodiment of any formula described herein, R2 is methyl, ethyl, or n-propyl.

In still another aspect, in any embodiment of any formula described herein, R4 is selected from an aryl group, such as phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

An aryl group is defined to be a single or multiple fused ring group where at least one ring is aromatic. A substituted aryl group is an aryl group where a hydrogen has been replaced by a heteroatom or heteroatom containing group. Examples of useful aryl groups include phenyl, benzyl, carbazolyl, naphthyl, and the like.

In still yet another aspect, in any embodiment of any formula described herein, R3, R5, R6, and R7 are all hydrogen.

In still yet another aspect, in any embodiment of any formula described herein, R3 is hydrogen.

In yet another aspect, in any embodiment of any formula described herein, T is represented by the formula, $(R^*_2G)_g$, where each G is C, Si, or Ge, g is 1 or 2, and each $R^*$ is, independently, hydrogen, halogen, C1 to C20 hydrocarbyl (such as methyl, ethyl, propyl, butyl, pentyl, hexyl, heptyl, octyl, nonyl, decyl, undecyl, or dodecyl) or a C1 to C20 substituted hydrocarbyl, and two or more $R^*$ can form a cyclic structure including aromatic, partially saturated, or saturated cyclic or fused ring system.

In another embodiment of the invention, T is a bridging group and is represented by $R'_2C$, $R'_2Si$, $R'_2Ge$, $R'_2CCR'_2$, $R'_2CCR'_2CR'_2$, $R'_2CCR'_2CR'_2CR'_2$, $R'C=CR'$, $R'C=CR'CR'_2$, $R'_2CCR'=CR'CR'_2$, $R'C=CR'CR'=CR'$, $R'C=CR'CR'_2CR'_2$, $R'_2CSiR'_2$, $R_2CSiR'_2CR'_2$, $R'_2SiCR'_2SiR'_2$, $R'C=CR'SiR'_2$, $R'_2CGeR'_2$, $R'_2GeR'_2$, $R'_2CGeR'_2CR'_2$, $R'_2GeCR'_2GeR'_2$, $R'_2SiGeR'_2$, $R'C=CR'GeR'_2$, $R'B$, $R'_2C—BR'$, $R'_2C—BR'—CR'_2$, $R'_2C—O—CR'_2$, $R'_2CR'_2C—O—CR'_2CR'_2$, $R'_2C—O—CR'_2CR'_2$, $R'_2C—O—CR'=CR'$, $R'_2C—S—CR'_2$, $R'_2CR'_2C—S—CR'_2CR'_2$, $R'_2C—S—CR'_2CR'_2$, $R'_2C—S—CR'=CR'$, $R'_2C—Se—CR'_2$, $R'_2CR_2C—Se—CR'_2CR'_2$, $R'_2C—Se—CR_2CR'_2$, $R'_2C—Se—CR'=CR'$, $R'_2C—N=CR'$, $R'_2C—NR'—CR'_2$, $R'_2C—NR'—CR'_2CR'_2$, $R'_2C—NR'—CR'=CR'$, $R'_2CR'_2C—NR'—CR'_2CR'_2$, $R'_2C—P=CR'$, or $R'_2C—PR'—CR'_2$ where each $R'$ is, independently, hydrogen or a C1 to C20 containing hydrocarbyl (such as methyl, ethyl, propyl, butyl, pentyl, hexyl, heptyl, octyl, nonyl, decyl, undecyl, or dodecyl), substituted hydrocarbyl, halocarbyl, substituted halocarbyl, silylcarbyl or germylcarbyl substituent and, optionally, two or more adjacent R' may join to form a substituted or unsubstituted, saturated, partially unsaturated or aromatic, cyclic or polycyclic substituent. Preferably, T is a bridging group comprising carbon or silica, such as dialkylsilyl, preferably T is selected from $CH_2$, $CH_2CH_2$, $C(CH_3)_2$, $SiMe_2$, $SiPh_2$ SiMePh, silylcyclobutyl $(Si(CH_2)_3)$, $(Ph)_2C$, $(p-(Et)_3SiPh)_2C$, and cyclopentasilylene $(Si(CH2)4)$ $(Si(CH_2)_4)$.

In a preferred embodiment of the invention in any embodiment of any formula described herein, T is represented by the formula $Ra_2J$, where J is C, Si, or Ge, and each Ra is, independently, hydrogen, halogen, C1 to C20 hydrocarbyl (such as methyl, ethyl, propyl, butyl, pentyl, hexyl, heptyl, octyl, nonyl, decyl, undecyl, or dodecyl) or a C1 to C20 substituted hydrocarbyl, and two Ra can form a cyclic structure including aromatic, partially saturated, or saturated cyclic or fused ring system.

In a preferred embodiment of the invention in any embodiment of any formula described herein T is $CH_2$, $CH_2CH_2$, $C(CH_3)_2$, $SiMe_2$, $SiPh_2$, $SiMePh$, $Si(CH_2)_3$, $Si(CH_2)_4$, or $Si(CH_2)_5$.

The metallocene compounds described herein are "asymmetric", meaning that they have no planes of symmetry. An asymmetric catalyst according to this invention is a metallocene compound comprising at least two organic ligands which differ in their chemical structure. Still more preferably, the asymmetric catalyst according to this invention is a metallocene compound comprising at least two organic ligands which differ in their chemical structure and the metallocene compound is free of C2-symmetry and/or any higher symmetry (one or more planes of symmetry). Preferably, the asymmetric metallocene compound, comprises only two different organic ligands, still more preferably comprises two organic ligands which are different and linked via a bridge. A ligand is considered different from another ligand if they differ by at least one atom. For example, "indenyl" is different from "2-methylindenyl."

Examples of preferred metallocene compounds include: Dimethylsilylene(2-methyl-4-phenyl-1-indenyl)(2,3,4,5-tetramethyl-1-cyclopentadienyl)titanium dichloride, Dimethylsilylene(2-methyl-4-phenyl-1-indenyl)(2,3,4,5-tetramethyl-1-cyclopentadienyl)zirconium dichloride, Dimethylsilylene(2-methyl-4-phenyl-1-indenyl)(2,3,4,5-tetramethyl-1-cyclopentadienyl)hafnium dichloride, Dimethylsilylene(2-methyl-4-phenyl-1-indenyl)(2,3,4,5-tetramethyl-1-cyclopentadienyl)zirconium dibromide, Dimethylsilylene(2-methyl-4-phenyl-1-indenyl)(2,3,4,5-tetramethyl-1-cyclopentadienyl)zirconium diiodide, Dimethylsilylene(2-methyl-4-phenyl-1-indenyl)(2,3,4,5-tetramethyl-1-cyclopentadienyl)zirconium dimethoxide, Dimethylsilylene(2-methyl-4-phenyl-1-indenyl)(2,3,4,5-tetramethyl-1-cyclopentadienyl)zirconium diethoxide, Dimethylsilylene(2-methyl-4-phenyl-1-indenyl)(2,3,4,5-tetramethyl-1-cyclopentadienyl)zirconium diisopropoxide, Dimethylsilylene(2-methyl-4-phenyl-1-indenyl)(2,3,4,5-tetramethyl-1-cyclopentadienyl)zirconium di-t-butoxide, Dimethylsilylene(2-methyl-4-phenyl-1-indenyl)(2,3,4,5-tetramethyl-1-cyclopentadienyl)zirconium bis(dimethylamide), Dimethylsilylene(2-methyl-4-phenyl-1-indenyl)(2,3,4,5-tetramethyl-1-cyclopentadienyl)zirconium bis(diethylamide), Dimethylsilylene(2-methyl-4-phenyl-1-indenyl)(2,3,4,5-tetramethyl-1-cyclopentadienyl)zirconium bis(diisopropylamide), Dimethylsilylene(2-methyl-4-phenyl-1-indenyl)(2,3,4,5-tetramethyl-1-cyclopentadienyl)zirconium bis(trifluoromethanesulfonate), Dimethylsilylene(2-methyl-4-phenyl-1-indenyl)(2,3,4,5-tetramethyl-1-cyclopentadienyl)zirconium bis(p-toluenesulfonate), Dimethylsilylene(2-methyl-4-phenyl-1-indenyl)(2,3,4,5-tetramethyl-1-cyclopentadienyl)zirconiumdimethyl, Dimethylsilylene(2-methyl-4-phenyl-1-indenyl)(2,3,4,5-tetramethyl-1-cyclopentadienyl)zirconiumdiethyl, Dimethylsilylene(2-methyl-4-phenyl-1-indenyl)(2,3,4,5-tetramethyl-1-cyclopentadienyl)zirconiumdibenzyl, Dimethylsilylene(2-methyl-4-phenyl-1-indenyl)(2,3,4,5-tetramethyl-1-cyclopentadienyl)zirconiumdiphenyl, Dimethylsilylene(2-methyl-4-phenyl-1-indenyl)(2,3,4,5-tetraethyl-1-cyclopentadienyl)zirconium dichloride, Dimethylsilylene(2-methyl-4-phenyl-1-indenyl)(2,3,4,5-tetrapropyl-1-cyclopentadienyl)zirconium dichloride, Dimethylsilylene(2-methyl-4-phenyl-1-indenyl)(3,4-dimethyl-1-cyclopentadienyl)zirconium dichloride, Dimethylsilylene(2-methyl-4-phenyl-1-indenyl)(3,4-diethyl-1-cyclopentadienyl)zirconium dichloride, Dimethylsilylene(2-methyl-4-phenyl-1-indenyl)(2-indenyl)zirconium dichloride, Dimethylsilylene(2-methyl-4-phenyl-1-indenyl)(1,3-dimethyl-2-indenyl)zirconium dichloride, Diethylsilylene(2-methyl-4-phenyl-1-indenyl)(2,3,4,5-tetramethyl-1-cyclopentadienyl)zirconium dichloride, Dipropylylsilylene(2-methyl-4-phenyl-1-indenyl)(2,3,4,5-tetramethyl-1-cyclopentadienyl)zirconium dichloride, Diphenylsilylene(2-methyl-4-phenyl-1-indenyl)(2,3,4,5-tetramethyl-1-cyclopentadienyl)zirconium dichloride, Silacyclebutylene(2-methyl-4-phenyl-1-indenyl)(2,3,4,5-tetramethyl-1-cyclopentadienyl)zirconium dichloride, Silacyclepentylene(2-methyl-4-phenyl-1-indenyl)(2,3,4,5-tetramethyl-1-cyclopentadienyl)zirconium dichloride, Dimethylgermylene(2-methyl-4-phenyl-1-indenyl)(2,3,4,5-tetramethyl-1-cyclopentadienyl)zirconium dichloride, Diethylgermylene(2-methyl-4-phenyl-1-indenyl)(2,3,4,5-tetramethyl-1-cyclopentadienyl)zirconium dichloride, Methylene(2-methyl-4-phenyl-1-indenyl)(2,3,4,5-tetramethyl-1-cyclopentadienyl)zirconium dichloride, Isopropylene(2-methyl-4-phenyl-1-indenyl)(2,3,4,5-tetramethyl-1-cyclopentadienyl)zirconium dichloride, Diphenylmethylene(2-methyl-4-phenyl-1-indenyl)(2,3,4,5-tetramethyl-1-cyclopentadienyl)zirconium dichloride, 1,2-Ethanediyl(2-methyl-4-phenyl-1-indenyl)(2,3,4,5-tetramethyl-1-cyclopentadienyl)zirconium dichloride, Dimethylsilylene(2,3-dimethyl-4-phenyl-1-indenyl)(2,3,4,5-tetramethyl-1-cyclopentadienyl)zirconium dichloride, Dimethylsilylene(2,5-dimethyl-4-phenyl-1-indenyl)(2,3,4,5-tetramethyl-1-cyclopentadienyl)zirconium dichloride, Dimethylsilylene(2,5,6-trimethyl-4-phenyl-1-indenyl)(2,3,4,5-tetramethyl-1-cyclopentadienyl)zirconium dichloride, Dimethylsilylene(2-methyl-4-phenyl-benz[f]-1-indenyl)(2,3,4,5-tetramethyl-1-cyclopentadienyl)zirconium dichloride, Dimethylsilylene(2-methyl-4-phenyl-benz[e]-1-indenyl)(2,3,4,5-tetramethyl-1-cyclopentadienyl)zirconium dichloride, Dimethylsilylene(2-methyl-4-phenyl-1-indacenyl)(2,3,4,5-tetramethyl-1-cyclopentadienyl)zirconium dichloride, Dimethylsilylene(2,6,6-trimethyl-4-phenyl-1-indacenyl)(2,3,4,5-tetramethyl-1-cyclopentadienyl)zirconium dichloride, Dimethylsilylene(2-ethyl-4-phenyl-1-indenyl)(2,3,4,5-tetramethyl-1-cyclopentadienyl)zirconium dichloride, Dimethylsilylene(2-propyl-4-phenyl-1-indenyl)(2,3,4,5-tetramethyl-1-cyclopentadienyl)zirconium dichloride, Dimethylsilylene(2-isobutyl-4-phenyl-1-indenyl)(2,3,4,5-tetramethyl-1-cyclopentadienyl)zirconium dichloride, Dimethylsilylene(2-neopentyl-4-phenyl-1-indenyl)(2,3,4,5-tetramethyl-1-cyclopentadienyl)zirconium dichloride, Dimethylsilylene(2-cyclohexylmethyl-4-phenyl-1-indenyl)(2,3,4,5-tetramethyl-1-cyclopentadienyl)zirconium dichloride, Dimethylsilylene(2-cyclopropyl-4-phenyl-1-indenyl)(2,3,4,5-tetramethyl-1-cyclopentadienyl)zirconium dichloride, Dimethylsilylene(2-methyl-4-(2-methyl)phenyl)-1-indenyl)(2,3,4,5-tetramethyl-1-cyclopentadienyl)zirconium dichloride, Dimethylsilylene(2-methyl-4-(3-methyl)phenyl)-1-indenyl)(2,3,4,5-tetramethyl-1-cyclopentadienyl)zirconium dichloride, Dimethylsilylene(2-methyl-4-(4-methyl)phenyl)-1-indenyl)(2,3,4,5-tetramethyl-1-cyclopentadienyl)zirconium dichloride, Dimethylsilylene(2-methyl-4-(3,5-dimethyl)phenyl)-1-indenyl)(2,3,4,5-tetramethyl-1-cyclopentadienyl)zirconium dichloride, Dimethylsilylene(2-methyl-4-(3,4,5-trimethyl)phenyl)-1-indenyl)(2,3,4,5-tetramethyl-1-cyclopentadienyl)zirconium dichloride, Dimethylsilylene(2-methyl-4-(4-t-butyl)phenyl)-1-indenyl)(2,3,4,5-tetramethyl-1-cyclopentadienyl)zirconium dichloride, Dimethylsilylene(2-methyl-4-(3,5-di-t-butyl)phenyl)-1-indenyl)(2,3,4,5-tetramethyl-1-cyclopentadienyl)zirconium dichloride, Dimethylsilylene(2-methyl-4-(1-naphthyl)-1-indenyl)(2,3,4,5-tetramethyl-1-cyclopentadienyl)zirconium dichloride, Dimethylsilylene(2-methyl-4-(2-naphthyl)-1-indenyl)(2,3,4,5-tetramethyl-1-cyclopentadienyl)zirconium dichloride, Dimethylsilylene(2-methyl-4-(2-biphenyl)-1-indenyl)(2,3,4,5-tetramethyl-1-cyclopentadienyl)zirconium dichloride, Dimethylsilylene(2-methyl-4-(3-biphenyl)-1-indenyl)(2,3,4,5-tetramethyl-1-cyclopentadienyl)zirconium dichloride, Dimethylsilylene(2-methyl-4-(4-biphenyl)-1-indenyl)(2,3,4,5-tetramethyl-1-cyclopentadienyl)zirconium dichloride, Dimethylsilylene(2-methyl-4-(4-trifluoromethylphenyl)-1-indenyl)(2,3,4,5-tetramethyl-1-cyclopentadienyl)zirconium dichloride, Dimethylsilylene(2-methyl-4-(3,5-bis(trifluoromethyl)phenyl)-1-indenyl)(2,3,4,5-tetramethyl-1-cyclopentadienyl)zirconium dichloride, Dimethylsilylene(2-methyl-4-(2-furanyl)-1-indenyl)(2,3,4,5-tetramethyl-1-cyclopentadienyl)zirconium dichloride, Dimethylsilylene(2-methyl-4-(5-methyl-2-furanyl)-1-indenyl)(2,3,4,5-tetramethyl-1-cyclopentadienyl)zirconium dichloride, Dimethylsilylene(2-methyl-4-(5-ethyl-2-furanyl)-1-indenyl)(2,3,4,5-tetramethyl-1-cyclopentadienyl)zirconium dichloride, Dimethylsilylene(2-methyl-4-(2-thiophenyl)-1-indenyl)(2,3,4,5-tetramethyl-1-cyclopentadienyl)zirconium dichloride, Dimethylsilylene(2-methyl-4-(5-methyl-2-thiophenyl)-1-indenyl)(2,3,4,5-tetramethyl-1-cyclopentadienyl)zirconium dichloride, and mixtures thereof.

Methods to Prepare the Catalyst Compounds

A general synthetic scheme is provided below to demonstrate how the catalysts are prepared.

Representative Synthesis

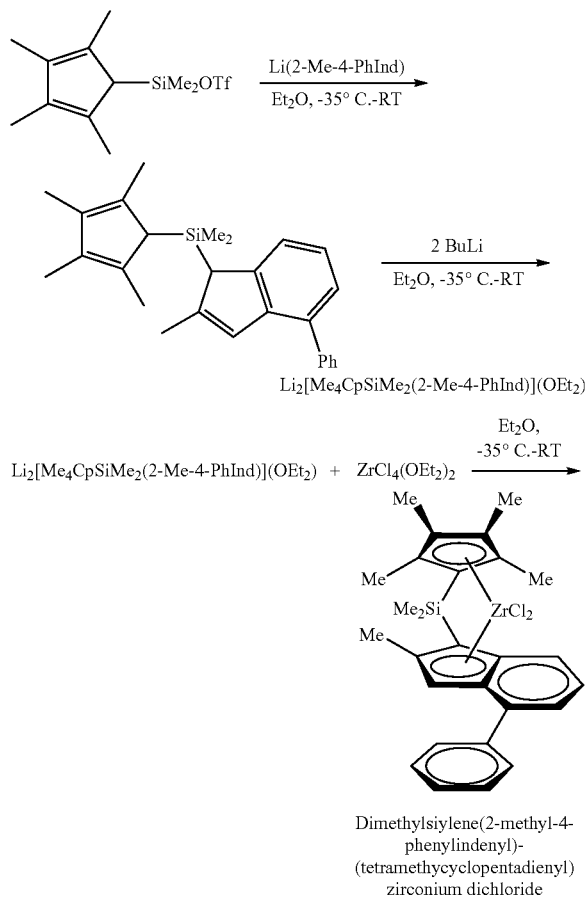

Dimethylsiylene(2-methyl-4-phenylindenyl)-(tetramethycyclopentadienyl)zirconium dichloride Activators The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally oligomeric compounds containing —Al(R1)-O— subunits, where R1 is an alkyl group. Examples of alumoxanes include methylalumoxane (MAO), modified methylalumoxane (MMAO), ethylalumoxane, and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis(pentafluorophenyl)borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 Å; EP 0 520 732 Å; EP 0 495 375 Å; EP 0 500 944 B1; EP 0 277 003 Å; EP 0 277 004 Å; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277 003 A1, and EP 0 277 004 A1:1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (II):

(II)

wherein Z is (L-H) or a reducible Lewis Acid, L is an neutral Lewis base; H is hydrogen; $(L-H)^+$ is a Bronsted acid; $A^{d-}$ is a non-coordinating anion having the charge d–; and d is an integer from 1 to 3.

When Z is (L-H) such that the cation component is (L-H)d+, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation (L-H)d+ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: (Ar3C+), where Ar is aryl or aryl substituted with a heteroatom, a C1 to C40 hydrocarbyl, or a substituted C1 to C40 hydrocarbyl, preferably the reducible Lewis acid is represented by the formula: (Ph3C+), where Ph is phenyl or phenyl substituted with a heteroatom, a C1 to C40 hydrocarbyl, or a substituted C1 to C40 hydrocarbyl. In a preferred embodiment, the reducible Lewis acid is triphenyl carbenium.

The anion component Ad– include those having the formula [Mk+Qn]d– wherein k is 1, 2, or 3; n is 1, 2, 3, 4, 5, or 6, preferably 3, 4, 5, or 6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable Ad– components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene and or propylene) with the catalyst compound, an optional chain transfer agent and a boron containing NCA activator represented by the formula (14):

(14)

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge $d^-$ (as further described above); d is 1, 2, or 3.

In a preferred embodiment in any NCA's represented by Formula 14 described above, the reducible Lewis acid is represented by the formula: (Ar3C+), where Ar is aryl or aryl substituted with a heteroatom, a C1 to C40 hydrocarbyl, or a substituted C1 to C40 hydrocarbyl, preferably the reducible Lewis acid is represented by the formula: (Ph3C+), where Ph is phenyl or phenyl substituted with a heteroatom, a C1 to C40 hydrocarbyl, or a substituted C1 to C40 hydrocarbyl.

In a preferred embodiment in any of the NCA's represented by Formula 14 described above, Zd+ is represented by the formula: (L-H)d+, wherein L is an neutral Lewis base; H is hydrogen; (L-H) is a Bronsted acid; and d is 1, 2, or 3, preferably (L-H)d+ is a Bronsted acid selected from ammoniums, oxoniums, phosphoniums, silyliums, and mixtures thereof.

In a preferred embodiment in any of the NCA's represented by Formula 14 described above, the anion component Ad– is represented by the formula [M*k*+Q*n*]d*– wherein k* is 1, 2, or 3; n* is 1, 2, 3, 4, 5, or 6 (preferably 1, 2, 3, or 4); n*–k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene and or propylene) with the catalyst compound, an optional chain transfer agent and an NCA activator represented by the formula (I):

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically, the NCA comprising an anion of Formula I also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula I described above, R is selected from the group consisting of substituted or unsubstituted C1 to C30 hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means C4 to C20 hydrocarbyl groups; —$SR_1$, —$N(R_2)_2$, and —$P(R_3)_2$, where each $R_1$, $R_2$, or $R_3$ is independently a substituted or unsubstituted hydrocarbyl as defined above; or a C1 to C30 hydrocarbyl substituted organometalloid.

In a preferred embodiment in any of the NCA's comprising an anion represented by Formula I described above, the NCA also comprises cation comprising a reducible Lewis acid represented by the formula: (Ar3C+), where Ar is aryl or aryl substituted with a heteroatom, a C1 to C40 hydrocarbyl, or a substituted C1 to C40 hydrocarbyl, preferably the reducible Lewis acid represented by the formula: (Ph3C+), where Ph is phenyl or phenyl substituted with a heteroatom, a C1 to C40 hydrocarbyl, or a substituted C1 to C40 hydrocarbyl.

In a preferred embodiment in any of the NCA's comprising an anion represented by Formula I described above, the NCA also comprises a cation represented by the formula, (L-H)d+, wherein L is an neutral Lewis base; H is hydrogen; (L-H) is a Bronsted acid; and d is 1, 2, or 3, preferably (L-H)d+ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

In a preferred embodiment of the invention, activators useful herein include: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated by reference herein.

In a preferred embodiment of the invention, activators useful herein include: N,N-dimethylanilinium tetrakis(perfluoronaphthyl)borate, N,N-dimethylanilinium tetrakis(perfluorobiphenyl)borate, N,N-dimethylanilinium tetrakis(3,5-bis (trifluoromethyephenyeborate, triphenylcarbenium tetrakis (perfluoronaphthyeborate, triphenylcarbenium tetrakis (perfluorobiphenyl)borate, triphenylcarbenium tetrakis(3,5-bis(trifluoromethyl)phenyeborate, triphenylcarbenium tetrakis(perfluorophenyl)borate, [$Ph_3C^+$][$B(C6F_5)_4^-$], [$Me_3NH^+$][$B(C6F_5)_4^-$]; 1-(4-(tris(pentafluorophenyeborate)-2,3,5,6-tetrafluorophenyl)pyrrolidinium; and tetrakis (pentafluorophenyeborate, 4-(tris(pentafluorophenyeborate)-2,3,5,6-tetrafluoropyridine.

In an embodiment of the invention, the activator comprises a triaryl carbonium (such as triphenylcarbenium tetraphenylborate, triphenylcarbenium tetrakis(pentafluorophenyl) borate, triphenylcarbenium tetrakis-(2,3,4,6-tetrafluorophenyl)borate, triphenylcarbenium tetrakis(perfluoronaphthyl) borate, triphenylcarbenium tetrakis(perfluorobiphenyl) borate, and triphenylcarbenium tetrakis(3,5-bis (trifluoromethyl)phenyl)borate).

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably, the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include Al2O3, ZrO2, SiO2, and combinations thereof, more preferably SiO2, Al2O3, or SiO2/Al2O3.

It is preferred that the support material, most preferably an inorganic oxide, has a surface area in the range of from about 10 to about 700 m2/g, pore volume in the range of from about 0.1 to about 4.0 cc/g and average particle size in the range of from about 5 to about 500 µm. More preferably, the surface area of the support material is in the range of from about 50 to about 500 m2/g, pore volume of from about 0.5 to about 3.5 cc/g and average particle size of from about 10 to about 200 µm. Most preferably, the surface area of the support material is in the range from about 100 to about 400 m2/g, pore volume from about 0.8 to about 3.0 cc/g and average particle size is from about 5 to about 100 µm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m2/gm; pore volume of 1.65 cm3/gm).

The support material should be dry, that is, free of absorbed water. Drying of the support material can be effected by heating or calcining at about 150° C. to about 1000° C., preferably at least about 200° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.1 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.1 hours to about 24 hours, from about 2 hours to about 16 hours, or from about 4 hours to about 8 hours. The slurry of the supported metallocene compound is then contacted with the activator solution.

The mixture of the metallocene, activator and support is heated to about 0° C. to about 70° C., preferably to about 23° C. to about 60° C., preferably at room temperature. Contact times typically range from about 0.1 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as propylene), and, optionally, comonomer, are contacted with a catalyst system comprising an activator and at least one metallocene compound, as described above. The catalyst compound and activator may be combined in any order, and are combined typically prior to contacting with the monomer.

Monomers useful herein include substituted or unsubstituted C2 to C40 alpha olefins, preferably C2 to C20 alpha olefins, preferably C2 to C12 alpha olefins, preferably ethylene, propylene, butene, pentene, hexene, heptene, octene, nonene, decene, undecene, dodecene, and isomers thereof. In a preferred embodiment of the invention, the monomer comprises propylene and an optional comonomers comprising one or more ethylene or C4 to C40 olefins, preferably C4 to C20 olefins, or preferably C6 to C12 olefins. The C4 to C40 olefin monomers may be linear, branched, or cyclic. The C4 to C40 cyclic olefins may be strained or unstrained, monocyclic or polycyclic, and may optionally include heteroatoms and/or one or more functional groups. In another preferred embodiment, the monomer comprises ethylene and an optional comonomers comprising one or more C3 to C40 olefins, preferably C4 to C20 olefins, or preferably C6 to C12 olefins. The C3 to C40 olefin monomers may be linear, branched, or cyclic. The C3 to C40 cyclic olefins may be strained or unstrained, monocyclic or polycyclic, and may optionally include heteroatoms and/or one or more functional groups.

Exemplary C2 to C40 olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated C4-10 alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably, the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably from about 20° C. to about 200° C., preferably from about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

Polyolefin Products

This invention also relates to compositions of matter produced by the methods described herein.

The process of this invention produces olefin polymers, preferably polyethylene and polypropylene homopolymers and copolymers. In a one embodiment, the polymers produced herein are copolymers of ethylene preferably having from 0 to 25 mole % (alternately from 0.5 to 20 mole %, alternately from 1 to 15 mole %, preferably from 3 to 10 mole %) of one or more C3 to C20 olefin comonomer (preferably C3 to C12 alpha-olefin, preferably propylene, butene, hexene, octene, decene, dodecene, preferably propylene, butene, hexene, octene), or are copolymers of propylene preferably having from 0 to 25 mole % (alternately from 0.5 to 20 mole %, alternately from 1 to 15 mole %, preferably from 3 to 10 mole %) of one or more of C2 or C4 to C20 olefin comonomer (preferably ethylene or C4 to C12 alpha-olefin, preferably ethylene, butene, hexene, octene, decene, dodecene, preferably ethylene, butene, hexene, octene).

Unless otherwise indicated Mw, Mn, MWD are determined by GPC as described in US 2006/0173123 pp. 24-25, paragraphs [0334] to [0341].

In a preferred embodiment of the invention, the propylene polymers produced may be isotactic polypropylene, atactic polypropylene and random, block or impact copolymers.

The polypropylene homopolymer or propylene copolymer produced herein may have some level of isotacticity, and is preferably isotactic or highly isotactic. As used herein, "isotactic" is defined as having at least 10% isotactic pentads according to analysis by 13C-NMR as described in US 2008/0045638 at paragraph [0613] et seq. As used herein, "highly isotactic" is defined as having at least 60% isotactic pentads according to analysis by 13C-NMR. In a desirable embodiment, a polypropylene homopolymer having at least 85% isotacticity, preferably least 90% isotacticity is produced herein. In another embodiment the propylene polymer produced may be atactic. Atactic polypropylene is defined to be less than 10% isotactic or syndiotactic pentads according to analysis by 13C-NMR.

Blends

In another embodiment, the polymer (preferably the polyethylene or polypropylene) produced herein is combined with one or more additional polymers prior to being formed into a film, molded part, or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

In other aspects, the embodiments of the invention described herein relate to:

1. A catalyst compound represented by the formula:

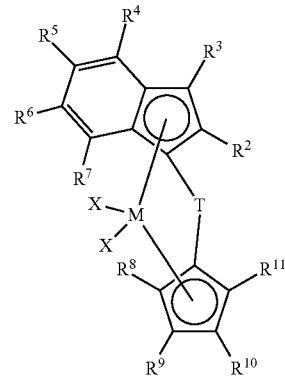

wherein

M is a transition metal atom selected from group 3, 4, or 5 of the Periodic Table of Elements, preferably a group 4 metal, preferably Hf, Ti or Zr;

T is a bridging group;

each X is a univalent anionic ligand, or two Xs are joined and bound to the metal atom to form a metallocycle ring, or two Xs are joined to form a chelating ligand, a diene ligand, or an alkylidene ligand;

$R^2$ is a substituted or unsubstituted $C_1$ to a $C_{20}$ hydrocarbyl group (such as methyl, ethyl, propyl, butyl, pentyl, hexyl, heptyl, octyl, nonyl, decyl, undecyl, or dodecyl), preferably $R^2$ is a primary substituted or unsubstituted $C_1$-$C_{12}$ alkyl group;

$R^3$, $R^5$, $R^6$, and $R^7$ are each independently a hydrogen atom or a substituted or unsubstituted $C_1$ to a $C_{20}$ alkyl group (such as methyl, ethyl, propyl, butyl, pentyl, hexyl, heptyl, octyl, nonyl, decyl, undecyl, or dodecyl) and any two of $R^5$, $R^6$, and $R^7$ adjacent to each other can be joined to form a cyclic structure, preferably $R^5$, $R^6$, and $R^7$ are independently a hydrogen atom or a substituted or unsubstituted $C_1$ to a $C_6$ hydrocarbyl group;

$R^4$ is a substituted or unsubstituted aryl group; and $R^8$, $R^9$, $R^{10}$ and $R^{11}$ are each independently a substituted or unsubstituted $C_1$ to a $C_6$ alkyl group (such as methyl, ethyl, propyl, butyl, pentyl, or hexyl) and $R^9$ and $R^{10}$ can be joined to form a cyclic structure. In one aspect, in any embodiment of any formula described herein, each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, preferably each X is a methyl group. Preferably, X is selected from chloro, bromo, methyl, ethyl, propyl, butyl, pentyl, hexyl, heptyl, octyl, nonyl, decyl, undecyl, and dodecyl.

2. The catalyst of paragraph 1, wherein $R^2$ is a primary substituted or unsubstituted $C_1$-$C_{12}$ alkyl group.

3. The catalyst of either paragraphs 1 or 2, wherein $R^4$ is selected from phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

4. The catalyst of any of paragraphs 1 through 3, wherein $R^3$ is a hydrogen atom.

5. The catalyst of any of paragraphs 1 through 4, wherein T is represented by the formula, $(R^*_2G)_g$, where each G is C, Si, or Ge, g is 1 or 2, and each R* is, independently, hydrogen, halogen, $C_1$ to $C_{20}$ hydrocarbyl or a $C_1$ to $C_{20}$ substituted hydrocarbyl, and two or more R* can form a cyclic structure including aromatic, partially saturated, or saturated cyclic or fused ring system.

6. The catalyst of any of paragraphs 1 through 5, wherein $R^5$, $R^6$, and $R^7$ are independently a hydrogen atom or a substituted or unsubstituted $C_1$ to a $C_6$ hydrocarbyl group, and any two of $R^5$, $R^6$, and $R^7$ can be joined to form a cyclic structure.

7. A catalyst system comprising an activator and the catalyst of any of paragraphs 1 to 6.

8. The catalyst system of paragraph 7, wherein the activator comprises methylalumoxane.

9. The catalyst system of paragraph 7 or 8, wherein the activator comprises a non-coordination anion.

10. The catalyst or catalyst system of any of paragraphs 1 through 9, further comprising a solid support.

11. The catalyst or catalyst system of paragraph 10, wherein the solid support is silica.

12. A process to prepare isotactic polypropylene comprising contacting propylene with the catalyst system of any of paragraphs 7 through 11 and obtaining isotactic polypropylene.

13. A process to prepare olefin polymer comprising contacting olefin with the catalyst system of any of paragraphs 7 through 11 and obtaining polyolefin.

Most metallocenes used to make highly isotactic polypropylene are symmetrical bridged bis(indenyl)metallocenes like rac-dimethylsilylbis(2-methyl-4-phenylindenyl)zirconium dichloride, or asymmetric bridged bis(indenyl)metallocenes like psuedo rac-dimethylsilyl(2-methyl-4-phenylindenyl)(2-isopropyl-4-phenylindenyl)zirconium dichloride. These metallocenes suffer from long, involved syntheses, and the requirement to separate rac and meso isomers that are generally made in equal amounts.

The asymmetrical metallocenes described herein make highly isotactic polypropylene. The asymmetric metallocene syntheses provided herein are shorter and less involved than the symmetric bis(indenyl) metallocenes, and produce only one isomer. These metallocenes are thus easier and less expensive to make in high yield.

Experimental

MAO is methyl alumoxane (30 wt % in toluene) obtained from Albemarle.

Catalyst 1 is supported Dimethylsilylene(2-methyl-4-phenylindenyl)(tetramethylcyclopentadienyl)zirconium dichloride.

Catalyst 2 is supported Dimethylsilylene(2-ethyl-4-phenylindenyl)(tetramethylcyclopentadienyl)zirconium dichloride.

Test Methods

Melt Flow Rate (MFR) was measured according to ASTM 1238 (230° C., 2.16 kg).

Melt Index (MI) was measured according to ASTM 1238 (190° C., 2.16 kg).

High Load Melt Index (HLMI) was measured according to ASTM 1238 (190° C., 21.6 kg).

$^1$H NMR

1H NMR data was collected at 23° C. in a 5 mm probe using a 400 MHz Bruker spectrometer with deuterated tetrachloroethane. Data was recorded using a maximum pulse width of 45°, 8 seconds between pulses and signal averaging either 8 or 16 transients. The spectrum were normalized to protonated tetrachloroethane in the deuterated tetrachloroethane, which is expected to show a peak at 6.0 ppm.

$^{13}$C-NMR spectroscopy

Polymer microstructure was determined by 13C-NMR spectroscopy, including the concentration of isotactic and syndiotactic diads ([m] and [r]), triads ([mm] and [rr]), and pentads ([mmmm] and [rrrr]). Samples were dissolved in d2-1,1,2,2-tetrachloroethane. Spectra were recorded at 125° C. using a NMR spectrometer of 75 or 100 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J.

Randall in "Polymer Sequence Determination, 13C-NMR Method", Academic Press, New York, 1977. The percent of methylene sequences of two in length, % (CH2)2, were calculated as follows: the integral of the methyl carbons between 14-18 ppm (which are equivalent in concentration to the number of methylenes in sequences of two in length) divided by the sum of the integral of the methylene sequences of one in length between 45-49 ppm and the integral of the methyl carbons between 14-18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Differential Scanning calorimetry (DSC)

Melting temperature (Tm) was measured using Differential Scanning calorimetry (DSC) using commercially available equipment such as a TA Instruments 2920 DSC. Typically, 6 to 10 mg of molded polymer or plasticized polymer is sealed in an aluminum pan and loaded into the instrument at room temperature. Melting data (first heat) is acquired by heating the sample to at least 30° C. above its melting temperature, typically 220° C. for polypropylene, at a heating rate of 10° C./min. The sample is held for at least 5 minutes at this temperature to destroy its thermal history. Crystallization data are acquired by cooling the sample from the melt to at least 50° C. below the crystallization temperature, typically −50° C. for polypropylene, at a cooling rate of 20° C./min. The sample is held at this temperature for at least 5 minutes, and finally heated at 10° C./min to acquire additional melting data (second heat). The endothermic melting transition (first and second heat) and exothermic crystallization transition are analyzed for onset of transition and peak temperature. The melting temperatures reported are the peak melting temperatures from the second heat unless otherwise specified. For polymers displaying multiple peaks, the melting point (or melting temperature) is defined to be the peak melting temperature (i.e., associated with the largest endothermic calorimetric response in that range of temperatures) from the DSC melting trace; likewise, the crystallization temperature is defined to be the peak crystallization temperature (i.e., associated with the largest exothermic calorimetric response in that range of temperatures) from the DSC crystallization trace.

Preparation of Chlorodimethyl(2-methyl-4-phenyl-1H-indenyl)silane

To a colorless solution of dichlorodimethylsilane (12.90 g, 100 mmol, 3.00 eq.) in ether (30 ml) at −30° C. was added lithium (2-methyl-4-phenylindenide) (7.07 g, 33.3 mmol, 1.00 equiv.) in portions to give a cloudy yellow mixture. The reaction was allowed to warm to room temperature and stirred for 4 hours, becoming cloudy white with precipitate. The mixture was evaporated under vacuum, leaving a white solid. The solid was extracted with pentane (40 ml), and the extract was filtered to give a light yellow solution and white solid. The solution was evaporated under vacuum, leaving a white solid. Yield 9.85 g (99%). 1H NMR(C6 D6): δ7.59 (d, 2H), 7.44 (m, 1H), 7.36 (m, 3H), 7.22 (m, 2H), 6.86 (d, 1H), 3.42 (d, 1H), 2.11 (d, 3H), 0.27 (s, 3H), −0.03 (s, 3H).

Preparation of Dimethyl(2-methyl-4-phenyl-1H-indenyl)(2,3,4,5-tetramethylcyclopentadienyl)silane To a light yellow solution of chlorodimethyl(2-methyl-4-phenyl-1H-indenyl)silane (9.40 g, 31.4 mmol, 1.00 eq.) in tetrahydrofuran (40 ml) at −30° C. was added sodium (tetramethylcyclopentadienide) (4.76 g, 33.0 mmol, 1.05 equiv.) in portions to give a cloudy orange solution. The reaction was allowed to warm to room temperature and stirred for 23 hours. The mixture was evaporated under vacuum, leaving an orange residue. The residue was extracted with pentane (50 ml) and the extract was filtered to give a bright yellow solution and yellow solid. The solution was evaporated under vacuum to yield thick, orange oil. Yield 10.16 g (84%). 1H NMR (C6D6): δ7.61 (d, 2H), 7.41 (m, 1H), 7.31 (m, 4H), 7.19 (m, 1H), 6.85 (s, 1H), 3.60, (s, 1H), 3.16 (br s, 1H), 2.00 (s, 3H), 1.93 (s, 3H), 1.88 (s, 3H), 1.82 (s, 6H), −0.23 (s, 3H), −0.24 (s, 3H).

Preparation of Dilithium[tetramethylcyclopentadienidedimethylsilyl(2-methyl-4-phenylindenide)etherate To a yellow-orange solution of dimethyl(2-methyl-4-phenyl-1H-indenyl)(2,3,4,5-tetramethylcyclopentadienyl)silane (10.06 g, 26.2 mmol, 1.00 eq.) in ether (40 ml) at −30° C. was added 2.63 M butyllithium in hexanes (20.5 ml, 53.9 mmol, 2.06 equiv.) to give an orange solution which quickly turned bright yellow with precipitate. The reaction was stirred 20 hours, and then filtered to give an orange solution and yellow-orange solid. The solid was washed with pentane (30 ml) and dried under vacuum. Yield 12.14 g (99%). 1H NMR (C6D6): δ 7.72 (dd, 2H), 7.49 (br s, 1H), 7.27 (t, 2H), 7.10 (m, 1H), 6.48 (t, 1H), 6.12, (s, 1H), 3.40 (q, 4H), 2.44 (s, 3H), 2.15 (s, 6H), 1.90 (s, 6H), 1.13 (t, 6H), 0.65 (br s, 6H).

Preparation of [Dimethylsilylene(2-methyl-4-phenylindenyl)(tetramethylcyclopentadienyl)zirconium dichloride To a white suspension of zirconium tetrachloride bis(etherate) (2.00 g, 5.25 mmol, 1.00 eq.) in ether (25 ml) at −30° C. was added dilithium[tetramethylcyclopentadienidedimethylsilyl(2-methyl-4-phenylindenide)etherate (2.47 g, 5.25 mmol, 1.00 equiv.) in portions to give a cloudy, dull yellow mixture that slowly turned bright yellow. The reaction was stirred 21 hours and then evaporated under vacuum, leaving yellow solid. The solid was extracted with dichloromethane (50 ml, then 2×10 ml) and the extracts were filtered to give a yellow-orange solution and dull yellow solid. The solution was evaporated under vacuum to yield yellow solid. The solid was washed with pentane (2×30 ml) and dried under vacuum. Yield 2.44 g (85%). 1H NMR (CD2Cl2): δ 7.71. (d, 2H), 7.60 (d, 1H), 7.46 (t, 2H), 7.41 (m, 1H), 7.29 (d, 1H), 7.06 (m, 1H), 7.01 (s, 1H), 2.29 (s, 3H), 2.08 (s, 3H), 1.98 (s, 3H), 1.92 (s, 3H), 1.88 (s, 3H), 1.23 (s, 3H), 1.12 (s, 3H).

Preparation of Dimethyl(2-ethyl-4-phenyl-1H-indenyl)(2,3,4,5-tetramethylcyclopentadienyl)silane To a green solution of dimethyl(2,3,4,5-tetramethylcyclopenta-2,4-dien-1-yl)silyl trifluoromethanesulfonate (7.50 g, 22.8 mmol, 1.00 eq.) in ether (25 mL) at −35° C. was added lithium (2-ethyl-4-phenylindenide) (5.53 g, 24.4 mmol, 1.07 equiv.) in portions to give a hazy yellow solution near room temperature. The reaction was stirred for 20 hours, then evaporated under vacuum, leaving a light yellow semi-solid. The residue was extracted with pentane (3×40 mL) and the extract was filtered to give a yellow solution and pale yellow-white solid. The solution was evaporated under vacuum to yield thick, yellow oil. Yield 9.28 g (102%). 1H NMR (C6D6): δ 7.64 (d, 2H), 7.43 (d, 1H), 7.35 (d, 1H), 7.29 (t, 2H), 7.19 (t, 2H), 6.95 (s, 1H), 3.74, (s, 1H), 3.17 (br s, 1H), 2.46 (m, 1H), 2.32 (m, 1H), 1.95 (s, 3H), 1.89 (s, 3H), 1.82 (s, 6H), 1.05 (t, 3H), −0.22 (s, 6H).

Preparation of Dilithium[tetramethylcyclopentadien-idedimethylsilyl(2-ethyl-4-phenylindenide) 0.80 etherate To a yellow solution of dimethyl(2-ethyl-4-phenyl-1H-indenyl)(2,3,4,5-tetramethylcyclopentadienyl)silane (9.25 g, 23.2 mmol, 1.00 eq.) in ether (35 mL) at −35° C. was added 2.56 M butyllithium in hexanes (18.5 mL, 47.4 mmol, 2.04 equiv.) to give a warm, orange solution that slowly turned red. The reaction was stirred 16 hours, and then evaporated under vacuum to give a golden-brown solid. The solid was washed with pentane (3×30 mL) and dried under vacuum. Yield 12.28 g (94%). 1H NMR (THF-d8): δ 7.74 (d, 2H), 7.48 (br s, 1H), 7.28 (t, 2H), 7.10 (m, 1H), 6.47 (m, 1H), 6.23, (s, 1H), 3.40 (q, 3.2H), 2.90 (q, 2H), 2.16 (s, 6H), 1.90 (s, 6H), 1.24 (t, 3H), 1.13 (t, 5.3H), 0.66 (br s, 6H).

Preparation of Dimethylsilylene(2-ethyl-4-phenylin-denyl)(tetramethylcyclopentadienyl)zirconium dichloride To a white suspension of zirconium tetrachloride bis(etherate) (2.00 g, 5.25 mmol, 1.00 eq.) in ether (25 mL) at −30° C. was added dilithium [tetramethylcyclopentadienid-edimethylsilyl(2-ethyl-4-phenylindenide) 0.80 etherate (2.46 g, 5.24 mmol, 1.00 equiv.) in portions to give a dull greenish mixture that slowly turned golden brown and then bright yellow. The reaction was stirred 21 hours and then evaporated under vacuum, leaving yellow solid. The solid was extracted with dichloromethane (40 mL, then 4×5 mL) and the extracts were filtered to give manila solid and an orange solution. The solution was evaporated under vacuum to yield yellow solid. The solid was washed with pentane (2×10 mL) and dried under vacuum. Yield 2.42 g (83%). 1H NMR (CD2Cl2): δ 7.68. (d, 2H), 7.62 (d, 1H), 7.48 (t, 2H), 7.39 (m, 1H), 7.30 (d, 1H), 7.07 (m, 2H), 2.67 (m, 1H), 2.57 (m, 1H), 2.06 (s, 3H), 1.97 (s, 3H), 1.91 (s, 3H), 1.88 (s, 3H), 1.23 (s, 3H), 1.15 (t, 3H), 1.11 (s, 3H).

Supported [Dimethylsilylene(2-methyl-4-phenylin-denyl)(tetramethylcyclopentadienyl)zirconium dichloride 30 wt % MAO in toluene (6.25 g, 32.3 mmol, 120 equiv.) and toluene (6.50 g) were combined and stirred 15 minutes to give a clear solution. To this MAO solution was added dimethylsilylene(2-methyl-4-phenylindenyl)(tetramethylcyclo-pentadienylzirconium dichloride (0.147 g, 0.27 mmol, 1.00 equiv.) to give an orange-red solution. The reaction was stirred 15 minutes and then Davison 948 silica (5.00 g, dried at 600° C.) was added. The orange solid was mixed 10 minutes and then dried under vacuum for 22 hours. Yield 6.87 g (98%) burnt-orange solid.

Supported Dimethylsilylene(2-ethyl-4-phenylinde-nyl)(tetramethylcyclopentadienyl)zirconium dichloride 30 wt % MAO in toluene (6.26 g, 32.4 mmol, 120 equiv.) and toluene (6.50 g) were combined and stirred 15 minutes to give a clear solution. To this MAO solution was added Dimethylsilylene(2-ethyl-4-phenylindenyl)(tetramethylcyclo-pentadienyl)zirconium dichloride (0.151 g, 0.27 mmol, 1.00 equiv.) to give a dark orange solution. The reaction was stirred 15 minutes and then Davison 948 silica (5.00 g, dried at 600° C.) was added. The orange solid was mixed 10 minutes and then dried under vacuum for 21 hours. Yield 6.85 g (97%) manila-orange solid.

Propylene Polymerizations

Supported catalyst (50 mg) and pentane (1 ml) were added to a catalyst tube. Pentane (10 ml) and trioctylaluminum (50 μl) were added to a scavenger cylinder. The scavenger cylinder and 500 ml propylene were added to a 1 L autoclave and the autoclave was heated to 70° C. The catalyst tube was injected to the autoclave with nitrogen. The autoclave was stirred 1 hour at 70° C., then the autoclave was cooled and the propylene was vented. The polymer was collected and dried under vacuum at 60° C. overnight.

Ethylene/1-Hexene Copolymerizations

Supported catalyst (25 mg) and pentane (1 ml) were added to a catalyst tube. 1-Hexene (15 ml) and tri-n-octylaluminum (50 μl) were added to a comonomer cylinder. The comonomer cylinder and isobutane (400 mL) were added to a 1 L autoclave with nitrogen and the autoclave was heated to 85° C. The isobutane solution was then saturated with ethylene at 110 psi (758 kPa) above the starting pressure at 85° C. The catalyst tube was injected to the autoclave with ethylene at 130 psi (896 kPa) above the starting pressure at 85° C. The autoclave was stirred 40 minutes at 85° C. and 130 psi (896 kPa) ethylene, then the autoclave was cooled and vented. The polymer was collected and dried under vacuum at 60° C. overnight.

Propylene Polymerizations

| Run | Catalyst | Polymer Yield (g) | Tm (° C.) (DSC) | MFR dg/min | Pentad [mmmm] ($^{13}$CNMR) |
|---|---|---|---|---|---|
| 1 | 1 | 71.94 | 148 | 4.88 | 0.9310 |
| 2 | 1 | 71.77 | 147 | 4.51 | .9322 |
| 3 | 1 | 69.01 | 148 | 4.77 | .9340 |
| 4 | 2 | 88.83 | 149 | ND | ND |
| 5 | 2 | 86.76 | 149 | ND | ND |
| 6 | 2 | 87.80 | 149 | ND | ND |

Catalyst 1 = supported Me$_2$Si(2-Me-4-PhInd)(Me$_4$Cp)ZrCl$_2$.
Catalyst 2 = supported Me$_2$Si(2-Et-4-PhInd)(Me$_4$Cp)ZrCl$_2$.
ND means not determined Ethylene/1-Hexene Copolymerizations

| Run | Catalyst | Polymer Yield (g) | HLMI (dg/min) | Mw (g/mol) $^1$HNMR |
|---|---|---|---|---|
| 7 | 1 | 71.94 | 0.20 | 313,590 |
| 8 | 1 | 75.11 | 0.22 | 302,309 |
| 9 | 1 | 86.40 | 0.26 | 307,619 |
| 10 | 2 | 59.86 | ND | ND |
| 11 | 2 | 65.18 | ND | ND |
| 12 | 2 | 62.22 | ND | ND |

Catalyst 1 = supported Me$_2$Si(2-Me-4-PhInd)(Me$_4$Cp)ZrCl$_2$.
Catalyst 2 = supported Me$_2$Si(2-Et-4-PhInd)(Me$_4$Cp)ZrCl$_2$.
ND means not determined.

Polymerizations demonstrate that the catalysts are highly active in making isotactic polypropylene and are also highly active in making linear low density polyethylene (LLDPE).

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise, whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

The invention claimed is:

1. A catalyst compound represented by the formula:

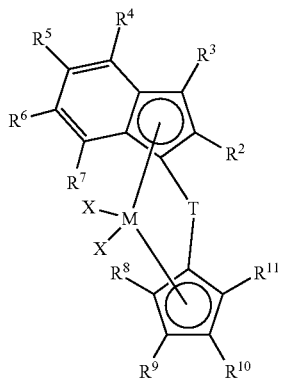

wherein
M is a transition metal atom selected from group 3, 4, or 5 of the Periodic Table of Elements;
T is a bridging group;
each X is a univalent anionic ligand, or two Xs are joined and bound to the metal atom to form a metallocycle ring, or two Xs are joined to form a chelating ligand, a diene ligand, or an alkylidene ligand;
$R^2$ is a substituted or unsubstituted $C_1$ to $C_{20}$ hydrocarbyl group;
$R^3$, $R^5$, $R^6$ and $R^7$ are each independently a hydrogen atom or a substituted or unsubstituted $C_1$ to $C_{20}$ hydrocarbyl group, and, optionally, any two of $R^5$, $R^6$, and $R^7$ can be joined to form a cyclic structure;
$R^4$ is a substituted or unsubstituted aryl group; and
$R^8$, $R^9$, $R^{10}$, and $R^{11}$ are each independently a substituted or unsubstituted $C_1$ to $C_6$ hydrocarbyl group and, optionally, $R^9$ and $R^{10}$ are joined to form a cyclic structure.

2. The catalyst compound of claim 1, wherein $R^2$ is a primary substituted or unsubstituted $C_1$-$C_{12}$ alkyl group.

3. The catalyst compound of claim 1, wherein $R^4$ is selected from phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

4. The catalyst compound of claim 1, wherein $R^3$ is a hydrogen atom.

5. The catalyst compound of claim 1, wherein T is represented by the formula, $(R^*_2G)_g$, where each G is C, Si, or Ge, g is 1 or 2, and each $R^*$ is, independently, hydrogen, halogen, $C_1$ to $C_{20}$ hydrocarbyl or a $C_1$ to $C_{20}$ substituted hydrocarbyl, and two or more $R^*$ can form a cyclic structure including aromatic, partially saturated, or saturated cyclic or fused ring system.

6. The catalyst compound of claim 1, wherein $R^5$, $R^6$, and $R^7$ are independently a hydrogen atom or a substituted or unsubstituted $C_1$ to $C_6$ hydrocarbyl group, and any two of $R^5$, $R^6$, and $R^7$ can be joined to form a cyclic structure.

7. A catalyst system comprising an activator and a catalyst represented by the formula:

wherein
M is a transition metal atom selected from group 3, 4, or 5 of the Periodic Table of Elements;
T is a bridging group;
each X is a univalent anionic ligand, or two Xs are joined and bound to the metal atom to form a metallocycle ring, or two Xs are joined to form a chelating ligand, a diene ligand, or an alkylidene ligand;
$R^2$ is a substituted or unsubstituted $C_1$ to $C_{20}$ hydrocarbyl group;
$R^3$, $R^5$, $R^6$, and $R^7$ are each independently a hydrogen atom or a substituted or unsubstituted $C_1$ to $C_{20}$ hydrocarbyl group, and, optionally, any two of $R^5$, $R^6$, and $R^7$ can be joined to form a cyclic structure;
$R^4$ is a substituted or unsubstituted aryl group; and
$R^8$, $R^9$, $R^{10}$, and $R^{11}$ are each independently a substituted or unsubstituted $C_1$ to $C_6$ hydrocarbyl group and, optionally, $R^9$ and $R^{10}$ are joined to form a cyclic structure.

8. The catalyst system of claim 7, wherein $R^2$ is a primary substituted or unsubstituted $C_1$-$C_{12}$ alkyl group.

9. The catalyst system of claim 7, wherein $R^4$ is selected from phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

10. The catalyst system of claim 7, wherein $R^3$ is a hydrogen atom.

11. The catalyst system of claim 7, wherein T is represented by the formula, $(R^*_2G)_g$, where each G is C, Si, or Ge, g is 1 or 2, and each $R^*$ is, independently, hydrogen, halogen, $C_1$ to $C_{20}$ hydrocarbyl or a $C_1$ to $C_{20}$ substituted hydrocarbyl, and two or more $R^*$ can form a cyclic structure including aromatic, partially saturated, or saturated cyclic or fused ring system.

12. The catalyst system of claim 7, wherein $R^5$, $R^6$, and $R^7$ are independently a hydrogen atom or a substituted or unsubstituted $C_1$ to $C_6$ hydrocarbyl group, and any two of $R^5$, $R^6$, and $R^7$ can be joined to form a cyclic structure.

13. The catalyst system of claim 7, wherein the activator comprises methylalumoxane.

14. The catalyst system of claim 7, wherein the activator comprises a non-coordinating anion.

15. A catalyst composition comprising a support and the catalyst compound of claim 1.

16. The catalyst composition of claim 15, wherein the support is silica.

17. A process to prepare isotactic polypropylene comprising contacting propylene with the catalyst system of claim 7 and obtaining isotactic polypropylene.

18. The catalyst system of claim 7, further comprising a support.

19. The catalyst system of claim 18, wherein the support is silica.

20. A process to prepare isotactic polymer comprising contacting C2 to C40 olefin monomers and optional C2 to C40 olefin comonomers with the catalyst system of claim 7 and obtaining polymer.

21. The process of claim 20, wherein the monomer comprises propylene and the comonomer comprises one or more of ethylene or C4 to C40 olefins.

* * * * *